US006895072B2

(12) United States Patent
Schrock et al.

(10) Patent No.: US 6,895,072 B2
(45) Date of Patent: May 17, 2005

(54) APPARATUS AND METHOD FOR NON-DESTRUCTIVE INSPECTION OF MATERIAL IN CONTAINERS

(75) Inventors: Todd H. Schrock, Kingston, TN (US); Adam R. Williamson, Seymour, TN (US); Richard L. Wyman, Knoxville, TN (US)

(73) Assignee: Heimann Systems Corp., Alcoa, TN (US)

( * ) Notice: Subject to any disclaimer, the term of this patent is extended or adjusted under 35 U.S.C. 154(b) by 53 days.

(21) Appl. No.: 10/629,868

(22) Filed: Jul. 30, 2003

(65) Prior Publication Data

US 2004/0240608 A1 Dec. 2, 2004

Related U.S. Application Data

(60) Provisional application No. 60/457,319, filed on Mar. 26, 2003.

(51) Int. Cl.[7] .............................................. G01N 23/04
(52) U.S. Cl. .......................................... 378/57; 378/62
(58) Field of Search .............................. 378/69, 62, 57, 378/51, 52, 58, 17, 41; 250/358.1, 359.1, 360.1; 99/451

(56) References Cited

U.S. PATENT DOCUMENTS

| | | | |
|---|---|---|---|
| 3,958,078 A | 5/1976 | Fowler et al. | |
| 4,350,889 A | 9/1982 | Lisnyansky | |
| 5,583,904 A | 12/1996 | Adams | |
| 5,805,662 A | 9/1998 | Kurbatov et al. | |
| 5,970,116 A | 10/1999 | Dueholm | |
| 6,005,912 A | 12/1999 | Ocleppo | |
| 6,359,961 B1 * | 3/2002 | Aufrichtig et al. | 378/41 |
| 6,434,217 B1 | 8/2002 | Pickelsimer et al. | |
| 6,449,334 B1 * | 9/2002 | Mazess et al. | 378/53 |
| 6,453,003 B1 * | 9/2002 | Springer et al. | 378/57 |
| 6,459,761 B1 | 10/2002 | Grodzins et al. | |

* cited by examiner

Primary Examiner—Edward J. Glick
Assistant Examiner—Hoon Song
(74) Attorney, Agent, or Firm—Foley & Lardner LLP

(57) ABSTRACT

An apparatus and method for non-destructive inspection of materials housed in containers (16) involves orienting an X-ray beam emitter (10) and detector (14) to direct and detect an X-ray beam (12) at an angle (34) lying in a range of from 8° to 20° to a conveying direction (22) of a conveyor (18) along which the materials are conveyed. The beam angle to the conveying direction works best between 8° and 12°, with an optimum being at approximately 10°. This arrangement de-emphasizes the leading and trailing edges of the containers while not substantially changing the image from that of a perpendicular beam, so that the detector images are still relatively easy to analyze. Thus, a one-detector system is adequate in many cases.

11 Claims, 2 Drawing Sheets

APPARATUS AND METHOD FOR NON-DESTRUCTIVE INSPECTION OF MATERIAL IN CONTAINERS

This non-provisional application claims priority under 35 U.S.C. 119(e) on Provisional Application No. 60/457,319, which was filed on Mar. 26, 2003 and is herein incorporated by reference.

BACKGROUND OF THE INVENTION

This invention concerns the non-destructive inspection of materials housed in containers, and more specifically the inspection of such materials using X-ray beams.

It is well-known to carry out non-destructive inspections of materials, including materials in containers, with X-ray beams. US Patents disclosing such apparatus and methods include: U.S. Pat. No. 3,958,078 to Fowler et al.; U.S. Pat. No. 4,350,889 to Lisnyansky; U.S. Pat. No. 5,583,904 to Adams; U.S. Pat. No. 5,805,662 to Kurbatov et al.; U.S. Pat. No. 5,970,116 to Dueholm; U.S. Pat. No. 6,005,912 to Ocleppo; U.S. Pat. No. 6,434,217 to Pickelsimer et al.; U.S. Pat. No. 6,449,334 to Mazess et al.; U.S. Pat. No. 6,453,003 to Springer et al.; and U.S. Pat. No. 6,459,761 to Grodzins et al.

A problem encountered when using such apparatus and systems, especially when inspecting food in containers, is that the geometry of the containers often causes undue lines in detector images thereof, which detract from the quality of such images and, therefore, negatively affect interpretations of the images. None of the apparatus and methods described in the above-mentioned patents adequately overcomes this problem.

A number of the systems described in these patents employ two or more X-ray beams at substantial angles to one another for producing two or more images that can be interpreted from the two different perspectives. This increases an amount of information available for interpreting the images. For example, Ocleppo (U.S. Pat. No. 6,005,912) describes a non-destructive X-ray inspection apparatus for the food industry that moves glass vessels to be examined along a conveyor. A single X-ray emitter produces two beams separated from one another by 90°, each being at a 45° angle to the conveyor, with each having a separate, angled, sensor. Thus, there are two sensors. The two angled sensors ensure that no area of food is detected by just one sensor, but rather will be detected by the two sensors at 90° to one another. Although this solution avoids erroneous lines that may appear in only one view, it is rather complicated and expensive, requiring at least two detectors and a relatively-complex interpretation of two images. Further, it is noted that this apparatus is specialized, in that it is for detecting of jars having particular types of concavities, which most food containers do not have.

It is noted that many X-ray apparatus and methods for inspecting food in containers respectively use only one X-ray beam and one detector so as not to unduly complicate structure and image interpretation. Similarly, many such X-ray inspection apparatus and methods that direct beams at conveyed containers, direct the beams perpendicular to conveying paths. Such a beam, perpendicular to the conveying path, provides a perspective that is most intuitive for image interpretation and that avoids passage of the beam through two adjacent types of materials and two adjacent containers. In this regard, bulk containers are often rectangular in shape, therefore having leading and trailing sides that are also perpendicular to the conveying path. When leading and trailing sides of adjacent containers are close together, an angled beam can pass through the two containers. Similarly, types of materials within the containers are aligned with these sides so that angled beams can pass through two adjacent types of materials.

In addition, such bulk containers often house smaller cases that also have sides perpendicular to the conveying path. Again, these perpendicular sides of the bulk containers and cases cause lines in detector images produced by perpendicular beams that detract from analysis of the detector images.

Thus, it is an object of this invention to provide an X-ray inspection apparatus (as well as a method) that produces an intuitive, easy-to-read detector image from a single X-ray beam of material in conveyed containers; but yet that reduces the effects of lines in the image caused by container sides, particularly for food containers.

SUMMARY OF THE INVENTION

According to principles of this invention, an apparatus and method for non-destructive inspection of materials housed in containers involves orienting an X-ray beam emitter and detector to direct and detect an X-ray beam at an angle within a range of from 8° to 20° inclusive to a conveying direction of a conveyor along which the materials are conveyed. Within this angle range, sides of the containers that are perpendicular to the conveying path, or direction, have a reduced effect on an image signal produced by the detector, while the image is still relatively easy to interpret, being close to that produced by a perpendicular beam. It appears that the angle of the beam to the conveying direction works best between 8° and 12° inclusive with the optimum being approximately 10°. This arrangement de-emphasizes the leading and trailing edges of the containers while not substantially changing the image from that of a perpendicular beam, so that the detector images are still relatively easy to analyze. Thus, a one-detector system is adequate in many cases.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages will be apparent from the following more particular description of preferred embodiments of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION OF THE INVENTION

Figure 1:
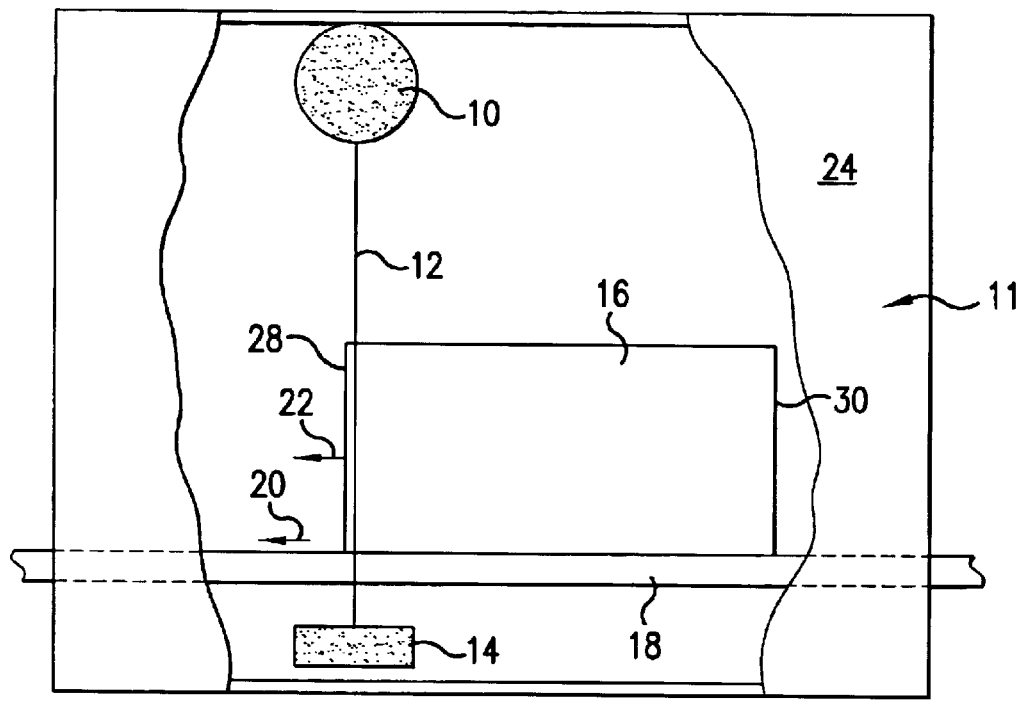
FIG. 1 depicts a side, cutaway, elevation of a prior-art X-ray inspection device of a general type with which this invention is used.

A prior-art X-ray inspection device 11 of the type normally used for inspecting food materials in containers includes an X-ray tube 10 for producing an X-ray beam 12, an X-ray detector 14 for receiving a transilluminated portion of the X-ray beam that has passed through a container 16 and generating therefrom an image signal representative of the transilluminated portion; a conveyor 18 for conveying the container 16 along a substantially straight conveying path 20 in a conveying direction 22; and a shielding tunnel 24. It is noted that in this prior-art system the conveying path and direction, 20 and 22, are substantially straight and that the X-ray beam emitter is mounted at a first fixed position adjacent the substantially straight conveying path. The detector 14 is mounted at a second position adjacent the conveying path on a side of the conveying path opposite to that of the first position at which the X-ray emitter 10 is located so that it can receive the transilluminated portion of the X-ray beam once it has passed through the container 16. It is further noted that the X-ray emitter 10 and the X-ray detector 14 are substantially directly opposite one another so that the X-ray beam 12 is substantially perpendicular to the conveying path 20 and the conveying direction 22.

In many such apparatus for inspecting food materials housed in containers there is only one X-ray beam and one detector, thereby reducing complexity and cost of the system and simplifying interpretation of only one detector image. In this regard, a representative detector image for the prior-art system of FIG. 1 is depicted in FIG. 3. As can be seen in FIG. 3, there are two distinct image lines 26 that are caused by a leading side 28 and a trailing side 30 of the container 16. It has been noticed that these lines can be disturbing when people or machines interpret the detector images 32 of the material in the container 16. In this respect, most large food material containers, as well as other types of containers, are rectangular in shape, and therefore have leading and trailing sides that are perpendicular to the conveying direction 22. At the same time, many bulk food-material containers also house smaller cases 34 having sides that are parallel to the leading and trailing sides, 28 and 30, as is shown in FIG. 2.

Figure 2:
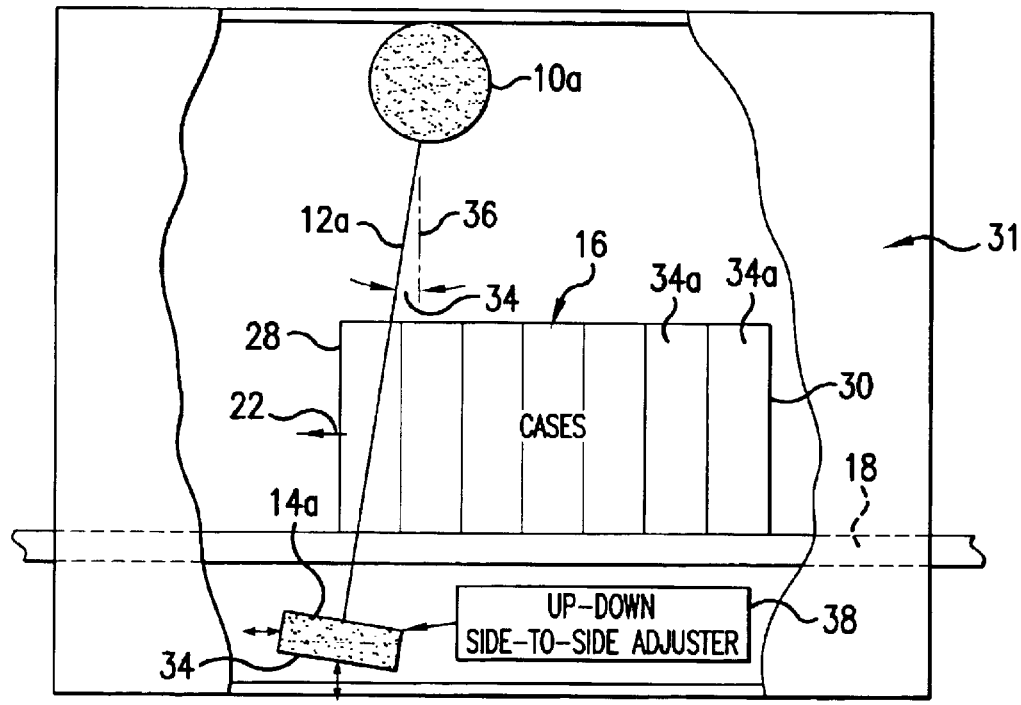
FIG. 2 depicts a side, cutaway, elevation of an X-ray inspection device employing structural features and method steps of this invention.
Figure 3:
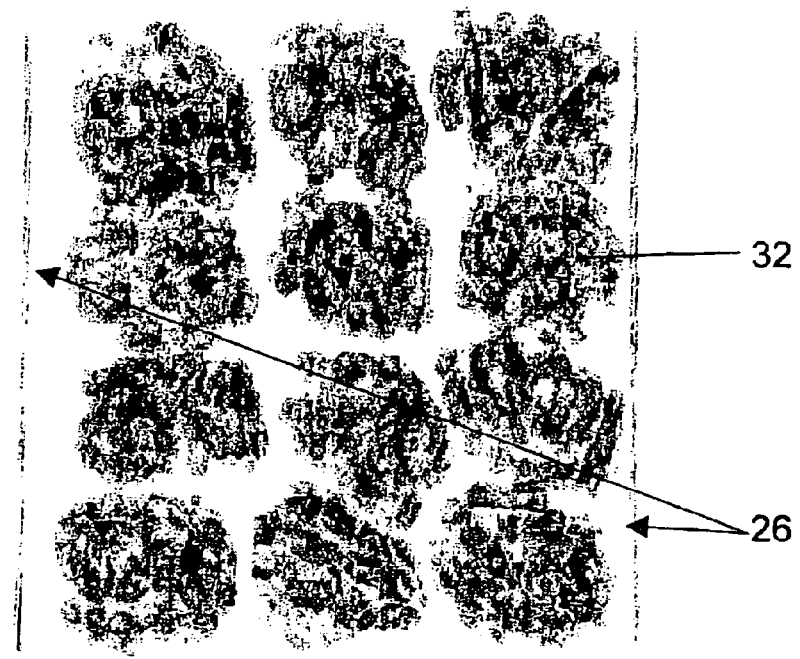
FIG. 3 depicts a prior-art image of a type normally produced with the device of FIG. 1.

With reference to FIG. 2, in an x-ray inspection device 31 of this invention, an X-ray emitter 10*a* is oriented to direct an X-ray beam 12A at an angle, 34 to a plane 36 that is perpendicular to the conveying direction 22, the angle 34 falling in a range of 8° to 20° inclusive. A detector 14*a* is also situated so that it is properly positioned and oriented to receive the angled X-ray beam. With regard to the angle 34, in the preferred embodiment, it is between 8° and 12° inclusive, with the best results being achieved at approximately 10°. In this respect, if the angle 34 is too great, the image is distorted from that of a perpendicular beam, with the beam unduly crossing adjacent containers and adjacent cases and objects within the containers. On the other hand, if the angle 34 is too small, the lines produced by perpendicular container sides are not sufficiently reduced.

An enhancement of this invention further involves an adjustment structure 38 that allows the X-ray detector 14*a* to be moved further away from the X-ray emitter 10*a* in order to provide magnification of an image generated by the X-ray detector 14*a* and that allows the X-ray detector 14*a* to be moved horizontally so as to fine-tune collimation. In this regard, it is noted that if the X-ray detector 14*a* is moved downwardly to increase magnification, it must also be moved sidewardly to ensure that it continues to align with the X-ray beam 12*a*.

Figure 4:
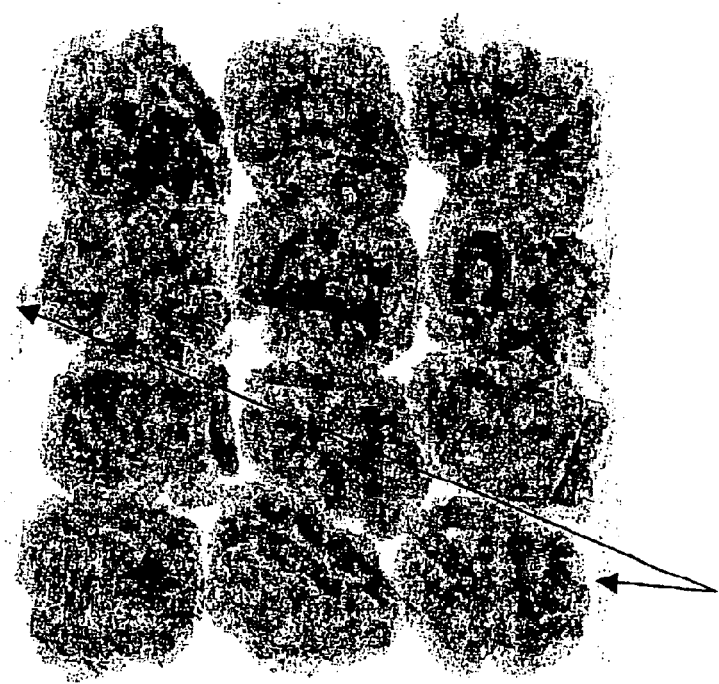
FIG. 4 depicts an image of a type normally produced by the X-ray inspection device of this invention and method.

The apparatus and method of this invention have the benefit that the image signals generated by the X-ray detector 14*a* are produced by a beam 12*a* that is sufficiently close to a perpendicular beam that an image thereof is not unduly modified from that of a perpendicular beam, as can be seen by comparing FIGS. 3 and 4. This enables one to interpret the image in substantially the same manner as is a perpendicular-beam image.

But it has the further advantage that the angle 34 at which the beam 12*a* is placed de-emphasizes image lines that are otherwise caused by leading and trailing sides 28 and 30 of the container 16, as well as leading and trailing sides 40 and 42 of cases 34*a* in the container 16. This reduces the amount of "noise" represented by the image lines 26 in an image signal generated by the X-ray detector 14, which more than compensates for any distortion caused by the angle.

While the invention has been particularly shown and described with reference to a preferred embodiment, it will be understood by those skilled in the art that various changes in form and detail may be made therein without departing from the spirit and scope of the invention.

For example, the X-ray tube 10*a* and the X-ray detector 14*a* need not be vertically above and below the conveyor 18 and the container 16, rather, they can be on horizontally opposite sides, as well as on other opposite sides. Similarly, it is possible for the X-ray tube 10 to be positioned forwardly of the X-ray detector 14*a*, relative to the conveying direction 22, rather than as is depicted in FIG. 2.

In a preferred embodiment, there is only one beam and one detector so that the image signals for only one image are involved. This simplifies analysis of the images and reduces the number of structural components. Further, it reduces the space required for the apparatus. However, it is also possible to have multiple beams and multiple detectors within the scope of this invention.

I claim:

1. Apparatus for non-destructively inspecting materials housed in containers, said apparatus comprising:
   a conveyor for conveying said containers along a conveying path in a conveying direction;
   an X-ray beam emitter mounted at a first position adjacent said conveying path for emitting an X-ray beam passing through said containers as they are conveyed along said conveying path;
   a detector mounted at a second position adjacent said conveying path on a side of said conveying path opposite that of said first position for receiving a transilluminated portion of the X-ray beam that has passed through said containers and generating therefrom an image signal representative of the transilluminated portion; and
   wherein said X-ray beam emitter is oriented to direct the X-ray beam at an angle to a plane perpendicular to the conveying direction, said angle lying in an angle range of 8° to 20° inclusive and wherein said detector is properly positioned and oriented to receive the angled X-ray beam.

2. Apparatus as in claim 1, wherein said angle range is from 8° to 12°, inclusive.

3. Apparatus as in claim 2, wherein said angle range is from 9° to 11°, inclusive.

4. Apparatus as in claim 3, wherein said angle is approximately 10°.

5. Apparatus as in claim 1, wherein said detector's position can be selectively adjusted toward and away from said conveying path as well as along a line parallel to said conveying path.

6. Apparatus as in claim 1, wherein there is only one beam emitter and one detector for the conveying path.

7. A method for the non-destructive inspection of material housed in containers, said method comprising:

conveying the containers along a conveying path;

passing an X-ray beam through said containers as they are conveyed along said conveying path;

receiving a transilluminated portion of the X-ray beam passed through said containers; and generating a signal representative of the transilluminated portion and therefore of an image representative of said material;

wherein said X-ray beam is directed at an angle to a plane perpendicular to the conveying path, said angle lying in an angle range of 8° to 20° inclusive.

8. A method as in claim 7, wherein said angle is in a range of 8° to 12°, inclusive.

9. A method as in claim 8, wherein said angle is in a range of 9° to 11°, inclusive.

10. A method as in claim 9, wherein said angle is approximately 10°.

11. A method as in claim 7, wherein there is only one X-ray beam and one detector along the conveying path for carrying out said method.

* * * * *